(12) United States Patent
Kim

(10) Patent No.: US 9,510,803 B2
(45) Date of Patent: Dec. 6, 2016

(54) PROVIDING COMPOUND IMAGE OF DOPPLER SPECTRUM IMAGES IN ULTRASOUND SYSTEM

(71) Applicant: SAMSUNG MEDISON CO., LTD., Gangwon-Do (KR)

(72) Inventor: Hyoung Jin Kim, Seoul (KR)

(73) Assignee: SAMSUNG MEDISON CO., LTD., Hongcheon-Gun, Gangwon-Do (KR)

( * ) Notice: Subject to any disclaimer, the term of this patent is extended or adjusted under 35 U.S.C. 154(b) by 455 days.

(21) Appl. No.: 13/730,033

(22) Filed: Dec. 28, 2012

(65) Prior Publication Data

US 2013/0172754 A1    Jul. 4, 2013

(30) Foreign Application Priority Data

Dec. 28, 2011 (KR) .......................... 10-2011-0144445

(51) Int. Cl.
*A61B 8/06* (2006.01)
*A61B 8/08* (2006.01)

(52) U.S. Cl.
CPC ................. *A61B 8/06* (2013.01); *A61B 8/488* (2013.01); *A61B 8/5253* (2013.01)

(58) Field of Classification Search
CPC .......... A61B 8/06; A61B 8/5253; A61B 8/488
See application file for complete search history.

(56) References Cited

U.S. PATENT DOCUMENTS

| | | | |
|---|---|---|---|
| 4,398,540 A * | 8/1983 | Takemura et al. | 600/441 |
| 2006/0030776 A1* | 2/2006 | Washburn et al. | 600/437 |
| 2006/0052704 A1* | 3/2006 | Baba et al. | 600/453 |
| 2007/0167790 A1 | 7/2007 | Kim et al. | |
| 2009/0149759 A1* | 6/2009 | Baba | A61B 8/06 600/454 |
| 2010/0260398 A1* | 10/2010 | Ma et al. | 382/131 |

FOREIGN PATENT DOCUMENTS

| | | |
|---|---|---|
| JP | 2007160120 A | 6/2007 |
| KR | 10-0271469 B1 | 1/2001 |
| KR | 10-2006-0115595 A | 11/2006 |
| KR | 10-0874550 B1 | 12/2008 |
| KR | 10-2010-060852 A | 6/2010 |

OTHER PUBLICATIONS

Stoylen, http://folk.ntnu.no/stoylen/strainrate/Ultrasound, Captured on Sep. 29, 2011, but the webpage was updated on Nov. 2010.*

(Continued)

*Primary Examiner* — Bo J Peng

(74) *Attorney, Agent, or Firm* — McDermott Will & Emery LLP

(57) ABSTRACT

There are provided embodiments for providing a compound image of Doppler spectrum images corresponding to at least two sample volumes. In one embodiment, by way of non-limiting example, an ultrasound system comprises: a processing unit configured to form at least two Doppler spectrum images corresponding to at least two sample volumes based on ultrasound data corresponding to the at least two sample volume, the processing unit being further configured to perform an image process for forming a compound image upon the at least two Doppler spectrum images to form the compound image.

19 Claims, 14 Drawing Sheets

(56) References Cited

OTHER PUBLICATIONS

Holly L. Gorton, Biological Action Spectra, http://photobiology.info/Gorton.html, Nov. 1, 2010.*
Korean Office Action Issued in Korean Application No. 10-2011-0144445 mailed May 15, 2013.
Korean Notice of Allowance with English translation issued in Korean Application No. 10-2011-0144445 issued on Nov. 28, 2013.

* cited by examiner

FIG. 4

$S_{1,t}$  $S_{2,t}$  $S_{3,t}$  $S_{4,t}$  $S_{5,t}$  $S_{6,t}$  $S_{7,t}$  $S_{8,t}$  $S_{9,t}$  $S_{10,t}$  $S_{11,t}$  $\cdots$  $S_{p,t}$ $\vdots$   $\vdots$   $\vdots$   $\vdots$   $\vdots$   $\vdots$   $\vdots$   $\vdots$   $\vdots$   $\vdots$   $\vdots$   $\vdots$   $\vdots$ $S_{1,6}$  $S_{2,6}$  $S_{3,6}$  $S_{4,6}$  $S_{5,6}$  $S_{6,6}$  $S_{7,6}$  $S_{8,6}$  $S_{9,6}$  $S_{10,6}$  $S_{11,6}$  $\cdots$  $S_{p,6}$
$S_{1,5}$  $S_{2,5}$  $S_{3,5}$  $S_{4,5}$  $S_{5,5}$  $S_{6,5}$  $S_{7,5}$  $S_{8,5}$  $S_{9,5}$  $S_{10,5}$  $S_{11,5}$  $\cdots$  $S_{p,5}$
$S_{1,4}$  $S_{2,4}$  $S_{3,4}$  $S_{4,4}$  $S_{5,4}$  $S_{6,4}$  $S_{7,4}$  $S_{8,4}$  $S_{9,4}$  $S_{10,4}$  $S_{11,4}$  $\cdots$  $S_{p,4}$
$S_{1,3}$  $S_{2,3}$  $S_{3,3}$  $S_{4,3}$  $S_{5,3}$  $S_{6,3}$  $S_{7,3}$  $S_{8,3}$  $S_{9,3}$  $S_{10,3}$  $S_{11,3}$  $\cdots$  $S_{p,3}$
$S_{1,2}$  $S_{2,2}$  $S_{3,2}$  $S_{4,2}$  $S_{5,2}$  $S_{6,2}$  $S_{7,2}$  $S_{8,2}$  $S_{9,2}$  $S_{10,2}$  $S_{11,2}$  $\cdots$  $S_{p,2}$
$S_{1,1}$  $S_{2,1}$  $S_{3,1}$  $S_{4,1}$  $S_{5,1}$  $S_{6,1}$  $S_{7,1}$  $S_{8,1}$  $S_{9,1}$  $S_{10,1}$  $S_{11,1}$  $\cdots$  $S_{p,1}$

| $CH_1$ | $CH_2$ | $CH_3$ | $CH_4$ | $CH_5$ | $CH_6$ | $CH_7$ | $CH_8$ | $CH_9$ | $CH_{10}$ | $CH_{11}$ | $\cdots$ | $CH_p$ |
|---|---|---|---|---|---|---|---|---|---|---|---|---|

| $P_{1,1}$ | $P_{1,2}$ | $P_{1,3}$ | $P_{1,4}$ | $P_{1,5}$ | $P_{1,6}$ | $P_{1,7}$ | $P_{1,8}$ | $P_{1,9}$ | $\cdots$ | $P_{1,N}$ |
|---|---|---|---|---|---|---|---|---|---|---|
| $P_{2,1}$ | $P_{2,2}$ | $P_{2,3}$ | $P_{2,4}$ | $P_{2,5}$ | $P_{2,6}$ | $P_{2,7}$ | $P_{2,8}$ | $P_{2,9}$ | $\cdots$ | $P_{2,N}$ |
| $P_{3,1}$ | $P_{3,2}$ | $P_{3,3}$ | $P_{3,4}$ | $P_{3,5}$ | $P_{3,6}$ | $P_{3,7}$ | $P_{3,8}$ | $P_{3,9}$ | $\cdots$ | $P_{3,N}$ |
| $P_{4,1}$ | $P_{4,2}$ | $P_{4,3}$ | $P_{4,4}$ | $P_{4,5}$ | $P_{4,6}$ | $P_{4,7}$ | $P_{4,8}$ | $P_{4,9}$ | $\cdots$ | $P_{4,N}$ |
| $P_{5,1}$ | $P_{5,2}$ | $P_{5,3}$ | $P_{5,4}$ | $P_{5,5}$ | $P_{5,6}$ | $P_{5,7}$ | $P_{5,8}$ | $P_{5,9}$ | $\cdots$ | $P_{5,N}$ |
| $P_{6,1}$ | $P_{6,2}$ | $P_{6,3}$ | $P_{6,4}$ | $P_{6,5}$ | $P_{6,6}$ | $P_{6,7}$ | $P_{6,8}$ | $P_{6,9}$ | $\cdots$ | $P_{6,N}$ |
| $P_{7,1}$ | $P_{7,2}$ | $P_{7,3}$ | $P_{7,4}$ | $P_{7,5}$ | $P_{7,6}$ | $P_{7,7}$ | $P_{7,8}$ | $P_{7,9}$ | $\cdots$ | $P_{7,N}$ |
| $\vdots$ | $\vdots$ | $\vdots$ | $\vdots$ | $\vdots$ | $\vdots$ | $\vdots$ | $\vdots$ | $\vdots$ | | $\vdots$ |
| $P_{M,1}$ | $P_{M,2}$ | $P_{M,3}$ | $P_{M,4}$ | $P_{M,5}$ | $P_{M,6}$ | $P_{M,7}$ | $P_{M,8}$ | $P_{M,9}$ | $\cdots$ | $P_{M,N}$ |

| $S_{1,t}$ | $S_{2,t}$ | $S_{3,t}$ | $S_{4,t}$ | $S_{5,t}$ | $S_{6,t}$ | $S_{7,t}$ | $S_{8,t}$ | $S_{9,t}$ | $S_{10,t}$ | $S_{11,t}$ | ... | $S_{p,t}$ |
|---|---|---|---|---|---|---|---|---|---|---|---|---|
| : | : | : | : | : | : | : | : | : | : | : | | : |
| $S_{1,6}$ | $S_{2,6}$ | $S_{3,6}$ | $S_{4,6}$ | $S_{5,6}$ | $S_{6,6}$ | $S_{7,6}$ | $S_{8,6}$ | $S_{9,6}$ | $S_{10,6}$ | $S_{11,6}$ | ... | $S_{p,6}$ |
| $S_{1,5}$ | $S_{2,5}$ | $S_{3,5}$ | $S_{4,5}$ | $S_{5,5}$ | $S_{6,5}$ | $S_{7,5}$ | $S_{8,5}$ | $S_{9,5}$ | $S_{10,5}$ | $S_{11,5}$ | ... | $S_{p,5}$ |
| $S_{1,4}$ | $S_{2,4}$ | $S_{3,4}$ | $S_{4,4}$ | $S_{5,4}$ | $S_{6,4}$ | $S_{7,4}$ | $S_{8,4}$ | $S_{9,4}$ | $S_{10,4}$ | $S_{11,4}$ | ... | $S_{p,4}$ |
| $S_{1,3}$ | $S_{2,3}$ | $S_{3,3}$ | $S_{4,3}$ | $S_{5,3}$ | $S_{6,3}$ | $S_{7,3}$ | $S_{8,3}$ | $S_{9,3}$ | $S_{10,3}$ | $S_{11,3}$ | ... | $S_{p,3}$ |
| $S_{1,2}$ | $S_{2,2}$ | $S_{3,2}$ | $S_{4,2}$ | $S_{5,2}$ | $S_{6,2}$ | $S_{7,2}$ | $S_{8,2}$ | $S_{9,2}$ | $S_{10,2}$ | $S_{11,2}$ | ... | $S_{p,2}$ |
| $S_{1,1}$ | $S_{2,1}$ | $S_{3,1}$ | $S_{4,1}$ | $S_{5,1}$ | $S_{6,1}$ | $S_{7,1}$ | $S_{8,1}$ | $S_{9,1}$ | $S_{10,1}$ | $S_{11,1}$ | ... | $S_{p,1}$ |
| $CH_1$ | $CH_2$ | $CH_3$ | $CH_4$ | $CH_5$ | $CH_6$ | $CH_7$ | $CH_8$ | $CH_9$ | $CH_{10}$ | $CH_{11}$ | ... | $CH_p$ |

| $P_{1,1}$ | $P_{1,2}$ | $P_{1,3}$ | $P_{1,4}$ | $P_{1,5}$ | $P_{1,6}$ | $P_{1,7}$ | $P_{1,8}$ | $P_{1,9}$ | ... | $P_{1,N}$ |
|---|---|---|---|---|---|---|---|---|---|---|
| $P_{2,1}$ | $P_{2,2}$ | $P_{2,3}$ | $P_{2,4}$ | $P_{2,5}$ | $P_{2,6}$ | $P_{2,7}$ | $P_{2,8}$ | $P_{2,9}$ | ... | $P_{2,N}$ |
| $P_{3,1}$ | $P_{3,2}$ | $P_{3,3}$ | $P_{3,4}$ | $P_{3,5}$ | $P_{3,6}$ | $P_{3,7}$ | $P_{3,8}$ | $P_{3,9}$ | ... | $P_{3,N}$ |
| $P_{4,1}$ | $P_{4,2}$ | $P_{4,3}$ | $P_{4,4}$ | $P_{4,5}$ | $P_{4,6}$ | $P_{4,7}$ | $P_{4,8}$ | $P_{4,9}$ | ... | $P_{4,N}$ |
| $P_{5,1}$ | $P_{5,2}$ | $P_{5,3}$ | $P_{5,4}$ | $P_{5,5}$ | $P_{5,6}$ | $P_{5,7}$ | $P_{5,8}$ | $P_{5,9}$ | ... | $P_{5,N}$ |
| $P_{6,1}$ | $P_{6,2}$ | $P_{6,3}$ | $P_{6,4}$ | $P_{6,5}$ | $P_{6,6}$ | $P_{6,7}$ | $P_{6,8}$ | $P_{6,9}$ | ... | $P_{6,N}$ |
| $P_{7,1}$ | $P_{7,2}$ | $P_{7,3}$ | $P_{7,4}$ | $P_{7,5}$ | $P_{7,6}$ | $P_{7,7}$ | $P_{7,8}$ | $P_{7,9}$ | ... | $P_{7,N}$ |
| : | : | : | : | : | : | : | : | : | | : |
| $P_{M,1}$ | $P_{M,2}$ | $P_{M,3}$ | $P_{M,4}$ | $P_{M,5}$ | $P_{M,6}$ | $P_{M,7}$ | $P_{M,8}$ | $P_{M,9}$ | ... | $P_{M,N}$ |

UI

PROVIDING COMPOUND IMAGE OF DOPPLER SPECTRUM IMAGES IN ULTRASOUND SYSTEM

CROSS-REFERENCE TO RELATED APPLICATIONS

The present application claims priority from Korean Patent Application No. 10-2011-0144445 filed on Dec. 28, 2011, the entire subject matter of which is incorporated herein by reference.

TECHNICAL FIELD

The present disclosure generally relates to ultrasound systems, and more particularly to providing a compound image of Doppler spectrum images in an ultrasound system.

BACKGROUND

An ultrasound system has become an important and popular diagnostic tool since it has a wide range of applications. Specifically, due to its non-invasive and non-destructive nature, the ultrasound system has been extensively used in the medical profession. Modern high-performance ultrasound systems and techniques are commonly used to produce two-dimensional or three-dimensional ultrasound images of internal features of target objects (e.g., human organs).

The ultrasound system may provide ultrasound images of various modes including a brightness mode image representing reflection coefficients of ultrasound signals (i.e., ultrasound echo signals) reflected from a target object of a living body with a two-dimensional image, a Doppler mode image representing velocity of a moving target object with spectral Doppler by using a Doppler effect, a color Doppler mode image representing velocity of the moving target object with colors by using the Doppler effect, an elastic image representing mechanical characteristics of tissues before and after applying compression thereto, and the like.

The ultrasound system may transmit the ultrasound signals to the living body and receive the ultrasound echo signals from the living body to form Doppler signals corresponding to a region of interest, which is set on the brightness mode image. The ultrasound system may further form the color Doppler mode image representing the velocity of the moving target object with colors based on the Doppler signals. In particular, the color Doppler image may represent the motion of the target object (e.g., blood flow) with the colors. The color Doppler image may be used to diagnose disease of a blood vessel, a heart and the like. However, it is difficult to represent an accurate motion of the target object (e.g., blood flow) since the respective colors indicated by a motion value is a function of the velocity of the target object, which moves forward in a transmission direction of the ultrasound signals and moves backward in the transmission direction of the ultrasound signals.

Particularly, the ultrasound system may set a sample volume on the brightness mode image, transmit ultrasound signals to the living body based on an ensemble number, and receive ultrasound echo signals from the living to form a Doppler spectrum image corresponding to the sample volume.

SUMMARY

There are provided embodiments for forming Doppler spectrum images corresponding to at least two sample volumes and compounding the Doppler spectrum images to provide a compound image.

In one embodiment, by way of non-limiting example, an ultrasound system comprises: a processing unit configured to form at least two Doppler spectrum images corresponding to at least two sample volumes based on ultrasound data corresponding to the at least two sample volume, the processing unit being further configured to perform an image process for forming a compound image upon the at least two Doppler spectrum images to form the compound image.

In another embodiment, there is provided a method of providing a compound image, comprising: a) forming at least two Doppler spectrum images corresponding to at least two sample volumes based on ultrasound data corresponding to the at least two sample volume; and b) performing an image process for forming a compound image upon the at least two Doppler spectrum images to form the compound image.

The Summary is provided to introduce a selection of concepts in a simplified form that are further described below in the Detailed Description. This Summary is not intended to identify key or essential features of the claimed subject matter, nor is it intended to be used in determining the scope of the claimed subject matter.

BRIEF DESCRIPTION OF THE DRAWINGS

FIG. 4 is a schematic diagram showing an example of sampling data and pixels of an ultrasound image.

FIG. 10 is a schematic diagram showing an example of setting a sampling data set.

DETAILED DESCRIPTION

A detailed description may be provided with reference to the accompanying drawings. One of ordinary skill in the art may realize that the following description is illustrative only and is not in any way limiting. Other embodiments of the present invention may readily suggest themselves to such skilled persons having the benefit of this disclosure.

Figure 1:
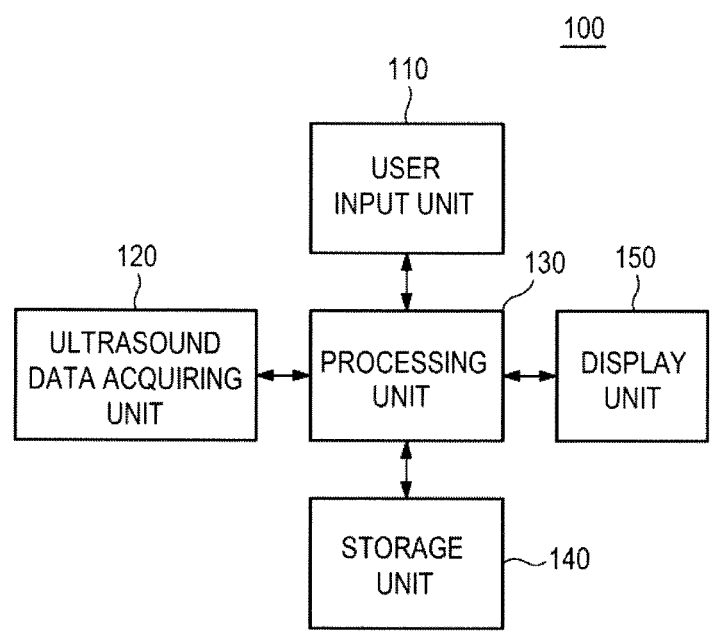
FIG. 1 is a block diagram showing an illustrative embodiment of an ultrasound system.

Referring to FIG. 1, an ultrasound system 100 in accordance with an illustrative embodiment is shown. As depicted therein, the ultrasound system 100 may include a user input unit 110.

Figure 2:
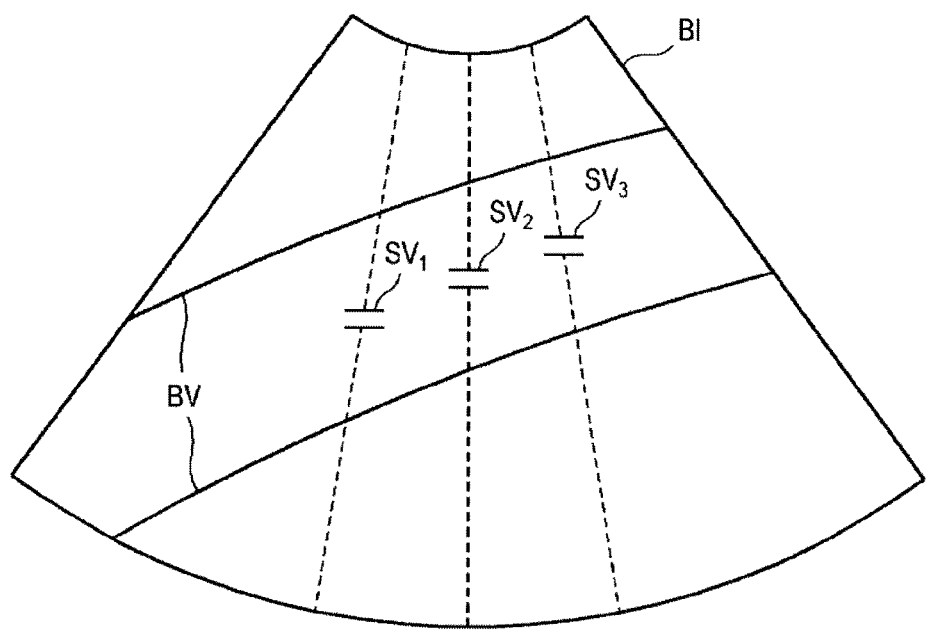
FIG. 2 is a schematic diagram showing an example of a brightness mode image and sample volumes.

The user input unit 110 may be configured to receive input information from a user. In one embodiment, the input information may include information for setting at least two sample volumes (e.g., $SV_1$, $SV_2$, $SV_3$) on a brightness mode image BI, as shown in FIG. 2. That is, the input information may include the number, position and size of the sample volumes. However, it should be noted herein that the input information may not be limited thereto. In FIG. 2, the reference numeral BV represents a blood vessel. The user input unit 110 may include a control panel, a track ball, a touch screen, a mouse, a keyboard and the like.

The ultrasound system 100 may further include an ultrasound data acquiring unit 120. The ultrasound data acquiring unit 120 may be configured to transmit ultrasound signals to a living body. The living body may include target objects (e.g., blood vessel, heart, blood flow, etc). The ultrasound data acquiring unit 120 may be further configured to receive ultrasound signals (i.e., ultrasound echo signals) from the living body to acquire ultrasound data corresponding to an ultrasound image.

Figure 3:
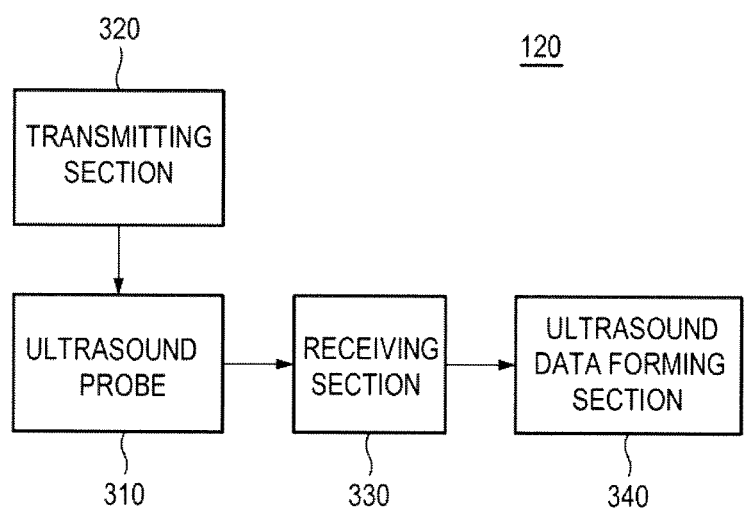
FIG. 3 is a block diagram showing an illustrative embodiment of an ultrasound data acquiring unit.

FIG. 3 is a block diagram showing an illustrative embodiment of the ultrasound data acquiring unit. Referring to FIG. 3, the ultrasound data acquiring unit 120 may include an ultrasound probe 310.

The ultrasound probe 310 may include a plurality of elements (not shown) for reciprocally converting between ultrasound signals and electrical signals. The ultrasound probe 310 may be configured to transmit the ultrasound signals to the living body. The ultrasound probe 310 may be further configured to receive the ultrasound echo signals from the living body to output electrical signals (hereinafter referred to as "reception signals"). The reception signals may be analog signals. The ultrasound probe 310 may include a convex probe, a linear probe and the like.

The ultrasound data acquiring unit 120 may further include a transmitting section 320. The transmitting section 320 may be configured to control the transmission of the ultrasound signals. The transmitting section 320 may be further configured to generate electrical signals (hereinafter referred to as "transmission signals") in consideration of the elements.

In one embodiment, the transmitting section 320 may be configured to generate transmission signals (hereinafter referred to as "brightness mode transmission signals") for obtaining the brightness mode image BI in consideration of the elements. Thus, the ultrasound probe 310 may be configured to convert the brightness mode transmission signals provided from the transmitting section 320 into the ultrasound signals, transmit the ultrasound signals to the living body, and receive the ultrasound echo signals from the living body to output reception signals (hereinafter referred to as "brightness mode reception signals").

The transmitting section 320 may be further configured to generate transmission signals (hereinafter referred to as "Doppler mode transmission signals") for obtaining Doppler spectrum images corresponding to the at least two sample volumes based on an ensemble number. The ensemble number may represent the number of transmitting and receiving the ultrasound signals. Thus, the ultrasound probe 310 may be configured to convert the Doppler mode transmission signals provided from the transmitting section 320 into the ultrasound signals and transmit the ultrasound signals to the living body. The ultrasound signals transmitted from the ultrasound probe 310 may be the plane wave signals. The ultrasound probe 310 may be further configured to receive the ultrasound echo signals from the living body in at least one reception direction to output reception signals (hereinafter referred to as "Doppler mode reception signals").

The ultrasound data acquiring unit 120 may further include a receiving section 330. The receiving section 330 may be configured to perform an analog-digital conversion upon the reception signals provided from the ultrasound probe 310 to form sampling data. The receiving section 330 may be also configured to perform a reception beam-forming upon the sampling data in consideration of the elements to form reception-focused data. The reception beam-forming will be described below in detail.

In one embodiment, the receiving section 330 may be configured to perform the analog-digital conversion upon the brightness mode reception signals provided from the ultrasound probe 310 to form sampling data (hereinafter referred to as "brightness mode sampling data"). The receiving section 330 may be further configured to perform the reception beam-forming upon the brightness mode sampling data to form reception-focused data (hereinafter referred to as "brightness mode reception-focused data").

The receiving section 330 may be further configured to perform the analog-digital conversion upon the Doppler mode reception signals provided from the ultrasound probe 310 to form sampling data (hereinafter referred to as "Doppler mode sampling data"). The receiving section 330 may be also configured to perform the reception beam-forming upon the Doppler mode sampling data to form reception-focused data (hereinafter referred to as "Doppler mode reception-focused data") corresponding to the at least two sample volumes.

For example, the receiving section 330 may perform the reception beam-forming upon the Doppler mode sampling data to form first Doppler mode reception-focused data corresponding to the sample volume $SV_1$. The receiving section 330 may further perform the reception beam-forming upon the Doppler mode sampling data to form second Doppler mode reception-focused data corresponding to the sample volume $SV_2$. The receiving section 330 may also perform the reception beam-forming upon the Doppler mode sampling data to form third Doppler mode reception-focused data corresponding to the sample volume $SV_3$.

The reception beam-forming may be described with reference to the accompanying drawings.

In one embodiment, the receiving section 330 may be configured to perform the analog-digital conversion upon the reception signals provided through a plurality of channels $CH_k$, wherein $1 \leq k \leq N$, from the ultrasound probe 310 to form sampling data $S_{i,j}$, wherein the i and j are a positive integer, as shown in FIG. 4. The sampling data $S_{i,j}$ may be stored in a storage unit 140. The receiving section 330 may be further configured to detect pixels corresponding to the sampling data based on positions of the elements and positions (orientation) of pixels of the ultrasound image UI with respect to the elements. That is, the receiving section 330 may select the pixels, which the respective sampling data are used as pixel data thereof, during the reception beam-forming based on the positions of the elements and the orientation of the respective pixels of the ultrasound image UI with respect to the elements. The receiving section 330 may be configured to cumulatively assign the sampling data corresponding to the selected pixels as the pixel data.

Figure 5:
FIGS. 5 to 8 are schematic diagrams showing examples of performing a reception beam-forming.
Figure 6:
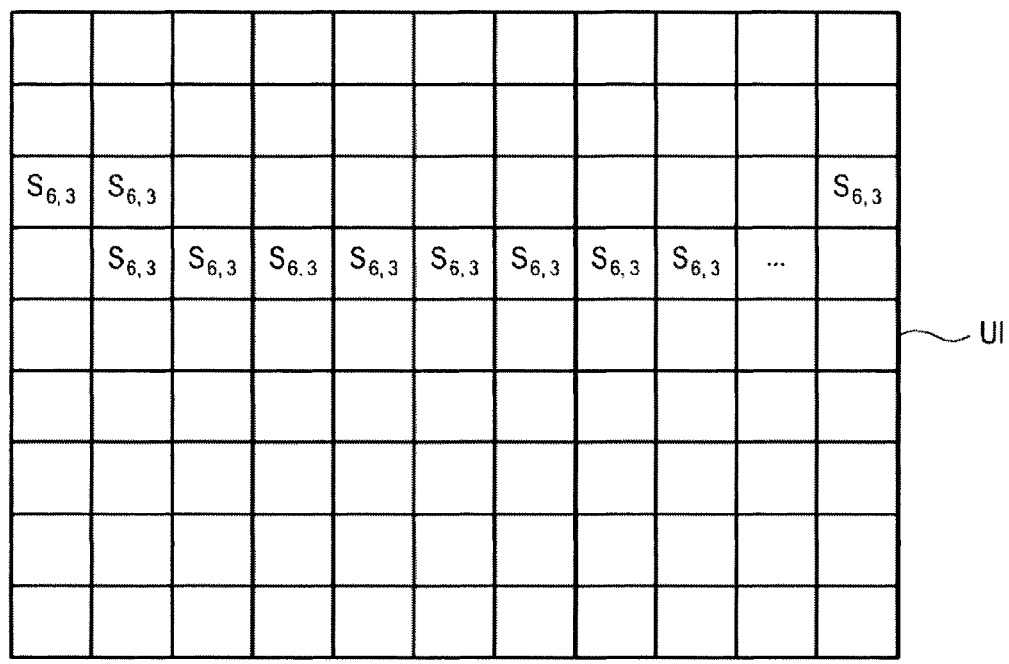

For example, the receiving section 330 may be configured to set a curve (hereinafter referred to as "reception beam-forming curve") $CV_{6,3}$ for selecting pixels, which the sampling data $S_{6,3}$ are used as the pixel data thereof, during the reception beam-forming based on the positions of the elements and the orientation of the respective pixels of the ultrasound image UI with respect to the elements, as shown in FIG. 5. The receiving section 330 may be further configured to detect the pixels $P_{3,1}$, $P_{3,2}$, $P_{4,2}$, $P_{4,3}$, $P_{4,4}$, $P_{4,5}$, $P_{4,6}$, $P_{4,7}$, $P_{4,8}$, $P_{4,9}$, ... $P_{3,N}$ corresponding to the reception beam-forming curve $CV_{6,3}$ from the pixels $P_{a,b}$ of the ultrasound image UI, wherein $1 \leq b \leq N$. That is, the receiving section 330 may select the pixels $P_{3,1}$, $P_{3,2}$, $P_{4,2}$, $P_{4,3}$, $P_{4,4}$, $P_{4,5}$, $P_{4,6}$, $P_{4,7}$, $P_{4,8}$, $P_{4,9}$, ... $P_{3,N}$ on which the reception beam-forming curve $CV_{6,3}$ passes among the pixels $P_{a,b}$ of the ultrasound image UI. The receiving section 330 may be also configured to assign the sampling data $S_{6,3}$ to the selected pixels $P_{3,1}$, $P_{3,2}$, $P_{4,2}$, $P_{4,3}$, $P_{4,4}$, $P_{4,5}$, $P_{4,6}$, $P_{4,7}$, $P_{4,8}$, $P_{4,9}$, ... $P_{3,N}$, as shown in FIG. 6.

Figure 7:
Figure 8:

Thereafter, the receiving section 330 may be configured to set a reception beam-forming curve $CV_{6,4}$ for selecting pixels, which the sampling data $S_{6,4}$ are used as the pixel data thereof, during the reception beam-forming based on the positions of the elements and the orientation of the respective pixels of the ultrasound image UI with respect to the elements, as shown in FIG. 7. The receiving section 330 may be further configured to detect the pixels $P_{2,1}$, $P_{3,1}$, $P_{3,2}$, $P_{4,2}$, $P_{4,3}$, $P_{4,4}$, $P_{5,4}$, $P_{5,5}$, $P_{5,6}$, $P_{5,7}$, $P_{5,8}$, $P_{4,9}$, $P_{5,9}$, ... $P_{4,N}$, $P_{3,N}$ corresponding to the reception beam-forming curve $CV_{6,4}$ from the pixels $P_{a,b}$ of the ultrasound image UI. That is, the receiving section 330 may select the pixels $P_{2,1}$, $P_{3,1}$, $P_{3,2}$, $P_{4,2}$, $P_{4,3}$, $P_{4,4}$, $P_{5,4}$, $P_{5,5}$, $P_{5,6}$, $P_{5,7}$, $P_{5,8}$, $P_{4,9}$, $P_{5,9}$, ... $P_{4,N}$, $P_{3,N}$ on which the reception beam-forming curve $CV_{6,4}$ passes among the pixels $P_{a,b}$ of the ultrasound image UI. The receiving section 330 may be further configured to assign the sampling data $S_{6,4}$ to the selected pixels $P_{2,1}$, $P_{3,1}$, $P_{3,2}$, $P_{4,2}$, $P_{4,3}$, $P_{4,4}$, $P_{5,4}$, $P_{5,5}$, $P_{5,6}$, $P_{5,7}$, $P_{5,8}$, $P_{5,9}$, ... $P_{4,N}$, $P_{3,N}$, as shown in FIG. 8. In this way, the respective sampling data, which are used as the pixel data, may be cumulatively assigned to the pixels as the pixel data.

The receiving section 330 may be configured to perform the reception beam-forming (i.e., summing) upon the sampling data, which are cumulatively assigned to the respective pixels $P_{a,b}$ of the ultrasound image UI to form the reception-focused data.

In another embodiment, the receiving section 330 may be configured to perform the analog-digital conversion upon the reception signals provided through the plurality of channels $CH_k$ from the ultrasound probe 310 to form the sampling data $S_{i,j}$, as shown in FIG. 4. The sampling data $S_{i,j}$ may be stored in the storage unit 140. The receiving section 330 may be further configured to detect pixels corresponding to the sampling data based on the positions of the elements and the position (orientation) of the pixels of the ultrasound image UI with respect to the elements. That is, the receiving section 330 may select the pixels, which the respective sampling data are used as the pixel data thereof, during the reception beam-forming based on the positions of the elements and the orientation of the respective pixels of the ultrasound image UI with respect to the elements. The receiving section 330 may be configured to cumulatively assign the sampling data corresponding to the selected pixels as the pixel data. The receiving section 330 may be further configured to determine pixels existing in the same column among the selected pixels. The receiving section 330 may be also configured to set weights corresponding to the respective determined pixels. The receiving section 330 may be additionally configured to apply the weights to the sampling data of the respective pixels.

Figure 9:
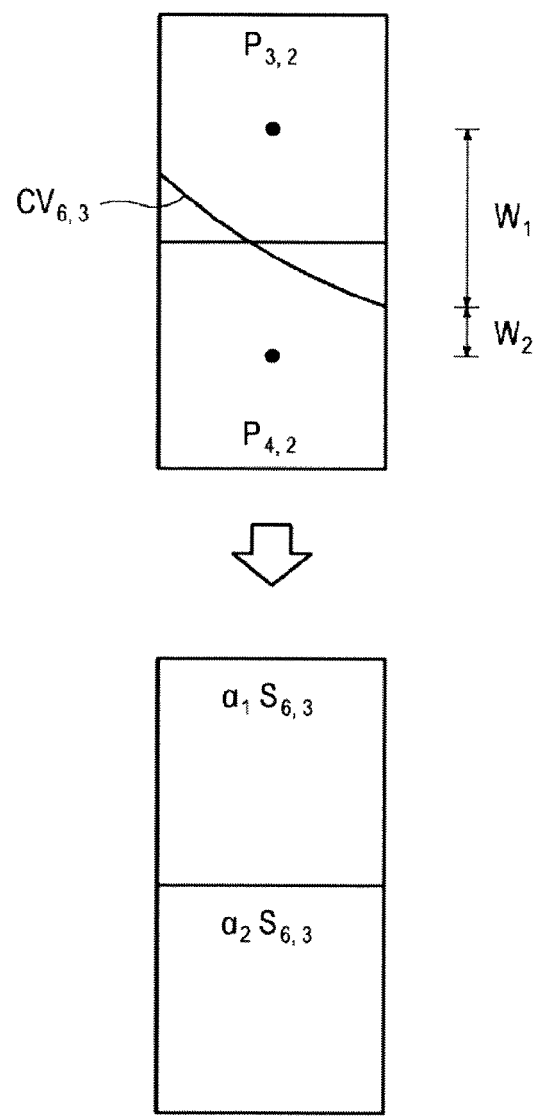
FIG. 9 is a schematic diagram showing an example of setting weights.

For example, the receiving section 330 may be configured to set the reception beam-forming curve $CV_{6,3}$ for selecting pixels, which the sampling data $S_{6,3}$ are used as the pixel data thereof, during the reception beam-forming based on the positions of the elements and the orientation of the respective pixels of the ultrasound image UI with respect to the elements, as shown in FIG. 5. The receiving section 330 may be further configured to detect the pixels $P_{3,1}$, $P_{3,2}$, $P_{4,2}$, $P_{4,3}$, $P_{4,4}$, $P_{4,5}$, $P_{4,6}$, $P_{4,7}$, $P_{4,8}$, $P_{4,9}$, ... $P_{3,N}$ corresponding to the reception beam-forming curve $CV_{6,3}$ from the pixels $P_{a,b}$ of the ultrasound image UI, wherein $1 \leq a \leq M$, $1 \leq b \leq N$. That is, the receiving section 330 may select the pixels $P_{3,1}$, $P_{3,2}$, $P_{4,2}$, $P_{4,3}$, $P_{4,4}$, $P_{4,5}$, $P_{4,6}$, $P_{4,7}$, $P_{4,8}$, $P_{4,9}$, ... $P_{3,N}$ on which the reception beam-forming curve $CV_{6,3}$ passes among the pixels $P_{a,b}$ of the ultrasound image UI. The receiving section 330 may be also configured to assign the sampling data $S_{6,3}$ to the selected pixels $P_{3,1}$, $P_{3,2}$, $P_{4,2}$, $P_{4,3}$, $P_{4,4}$, $P_{4,5}$, $P_{4,6}$, $P_{4,7}$, $P_{4,8}$, $P_{4,9}$, ... $P_{3,N}$, as shown in FIG. 6. The receiving section 330 may be further configured to determine pixels $P_{3,2}$ and $P_{4,2}$, which exist in the same column among the selected pixels $P_{3,1}$, $P_{3,2}$, $P_{4,2}$, $P_{4,3}$, $P_{4,4}$, $P_{4,5}$, $P_{4,6}$, $P_{4,7}$, $P_{4,8}$, $P_{4,9}$, ... $P_{3,N}$. The receiving section 330 may be further configured to calculate a distance $W_1$ from a center of the determined pixel $P_{3,2}$ to the reception beam-forming curve $CV_{6,3}$ and a distance $W_2$ from a center of the determined pixel $P_{4,2}$ to the reception beam-forming curve $CV_{6,3}$, as shown in FIG. 9. The receiving section 330 may be additionally configured to set a first weight $\alpha_1$ corresponding to the pixel $P_{3,2}$ based on the distance $W_1$ and a second weight $\alpha_2$ corresponding to the pixel $P_{4,2}$ based on the distance $W_2$. The first weight $\alpha_1$ and the second weight $\alpha_2$ may be set to be in proportional to or in inverse proportional to the calculated distances. The receiving section 330 may be further configured to apply the first weight $\alpha_1$ to the sampling data $S_{6,3}$ assigned to the pixel $P_{3,2}$ and to apply the second weight $\alpha_2$ to the sampling data $S_{6,3}$ assigned to the pixel $P_{4,2}$. The receiving section 330 may be configured to perform the above process upon the remaining sampling data.

The receiving section 330 may be configured to perform the reception beam-forming upon the sampling data, which are cumulatively assigned to the respective pixels $P_{a,b}$ of the ultrasound image UI to form the reception-focused data.

In yet another embodiment, the receiving section 330 may be configured to perform the analog-digital conversion upon the reception signals provided through the plurality of channels $CH_k$ from the ultrasound probe 310 to form the sampling data $S_{i,j}$, as shown in FIG. 4. The sampling data $S_{i,j}$ may be stored in the storage unit 140. The receiving section 330 may be further configured to set a sampling data set based on the sampling data $S_{i,j}$. That is, The receiving section 330 may set the sampling data set for selecting pixels, which the sampling data $S_{i,j}$ are used as the pixel data thereof, during the reception beam-forming.

For example, the receiving section 330 may be configured to set the sampling data $S_{1,1}$, $S_{1,4}$, ... $S_{1,t}$, $S_{2,1}$, $S_{2,4}$, ... $S_{2,t}$, ... $S_{p,t}$ as the sampling data set (denoted by a box) for selecting the pixels, which the sampling data S are used as the pixel data thereof, during the reception beam-forming, as shown in FIG. 10.

The receiving section 330 may be further configured to detect the pixels corresponding to the respective sampling data of the sampling data set based on the positions of the elements and the positions (orientation) of the respective pixels of the ultrasound image UI with respect to the elements. That is, the receiving section 330 may select the pixels, which the respective sampling data of the sampling data set are used as the pixel data thereof, during the reception beam-forming based on the positions of the elements and the orientation of the respective pixels of the ultrasound image UI with respect to the elements. The receiving section 330 may be further configured to cumulatively assign the sampling data to the selected pixels in the same manner with the above embodiments. The receiving section 330 may be also configured to perform the reception beam-forming upon the sampling data, which are cumulatively assigned to the respective pixels of the ultrasound image UI to form the reception-focused data.

In yet another embodiment, the receiving section 330 may be configured to perform a down-sampling upon the reception signals provided through the plurality of channels $CH_k$ from the ultrasound probe 310 to form down-sampling data. As described above, the receiving section 330 may be further configured to detect the pixels corresponding to the respective sampling data, based on the positions of the elements and the positions (orientation) of the respective pixels of the ultrasound image UI with respect to the elements. That is, the receiving section 330 may select the pixels, which the respective sampling data are used as the pixel data thereof, during the reception beam-forming based on the positions of the elements and the orientation of the pixels of the ultrasound image UI with respect to the elements. The receiving section 330 may be further configured to cumulatively assign the respective sampling data to the selected pixels in the same manner of the above embodiments. The receiving section 330 may be further configured to perform the reception beam-forming upon the sampling data, which are cumulatively assigned to the respective pixels of the ultrasound image UI to form the reception-focused data.

However, it should be noted herein that the reception beam-forming may not be limited thereto.

Referring back to FIG. 3, the ultrasound data acquiring unit 120 may further include an ultrasound data forming section 340. The ultrasound data forming section 340 may be configured to form the ultrasound data corresponding to the ultrasound image based on the reception-focused data provided from the receiving section 330. The ultrasound data forming section 340 may be further configured to perform a signal process (e.g., gain control, etc) upon the reception-focused data.

In one embodiment, the ultrasound data forming section 340 may be configured to form ultrasound data (hereinafter referred to as "brightness mode ultrasound data") corresponding to the brightness mode image BI based on the brightness mode reception-focused data provided from the receiving section 330. The brightness mode ultrasound data may include radio frequency data. However, it should be noted herein that the brightness mode ultrasound data may not be limited thereto.

The ultrasound data forming section 340 may be further configured to form ultrasound data (hereinafter referred to as "Doppler mode ultrasound data") corresponding to the at least two sample volumes based on the Doppler mode reception-focused data provided from the receiving section 330. The Doppler mode ultrasound data may include in-phase/quadrature data. However, it should be noted herein that the Doppler mode ultrasound data may not be limited thereto.

For example, the ultrasound data forming section 340 may form first Doppler mode ultrasound data corresponding to the sample volume $SV_1$ based on the first Doppler mode reception-focused data provided from the receiving section 330. The ultrasound data forming section 340 may further form second Doppler mode ultrasound data corresponding to the sample volume $SV_2$ based on the second Doppler mode reception-focused data provided from the receiving section 330. The ultrasound data forming section 340 may further form third Doppler mode ultrasound data corresponding to the sample volume $SV_3$ based on the third Doppler mode reception-focused data provided from the receiving section 330.

Referring back to FIG. 1, the ultrasound system 100 may further include a processing unit 130 in communication with the user input unit 110 and the ultrasound data acquiring unit 120. The processing unit 130 may include a central processing unit, a microprocessor, a graphic processing unit and the like.

Figure 11:
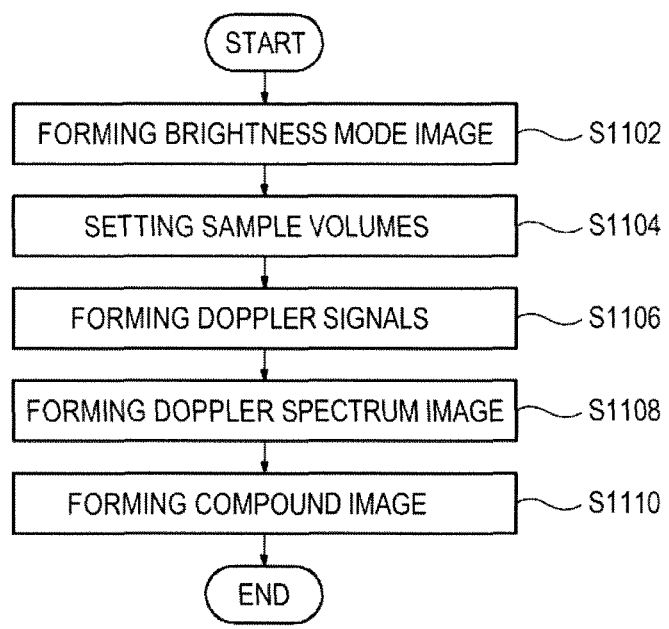
FIG. 11 is a flow chart showing a process of forming a compound image of Doppler spectrum images.
Figure 12:
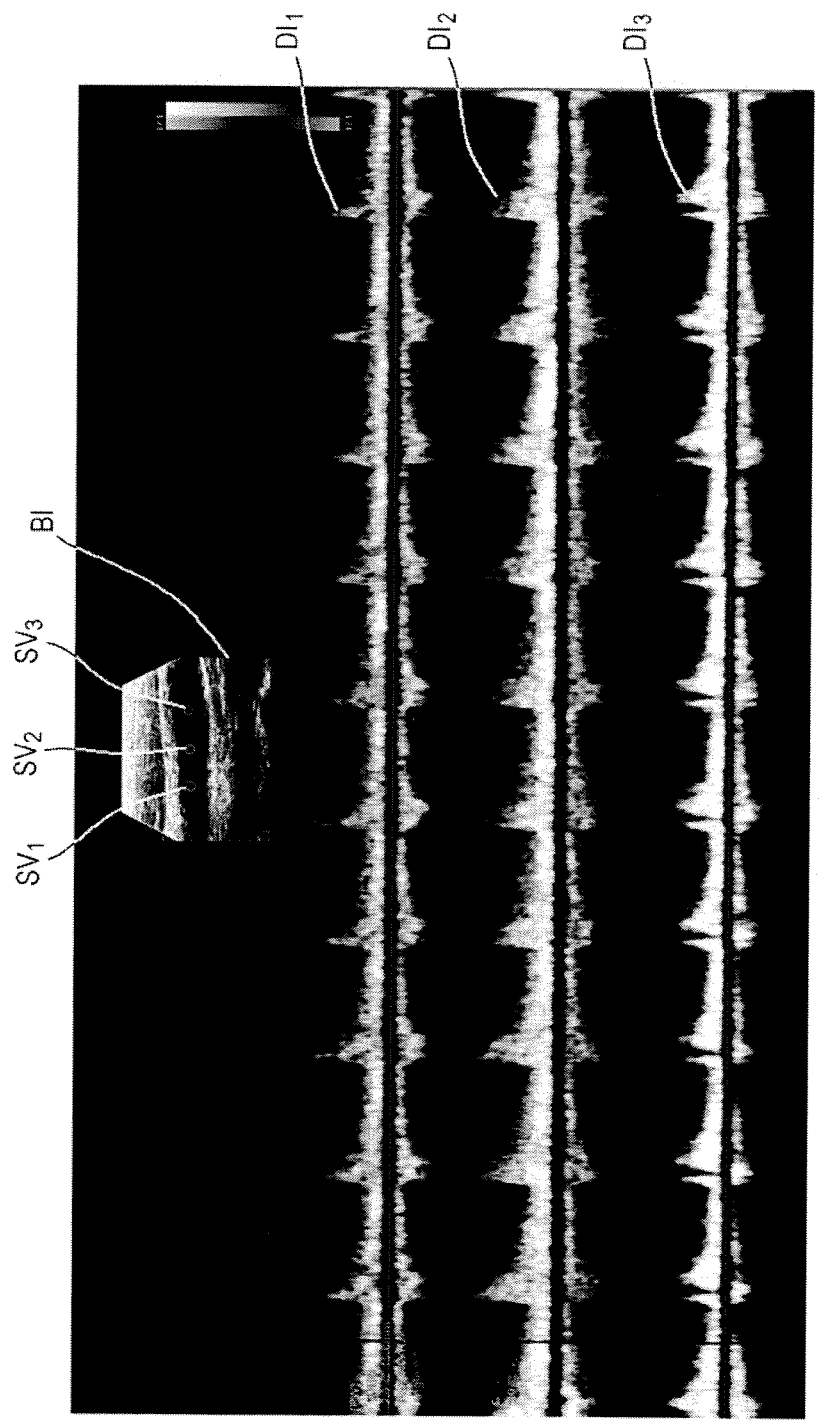
FIG. 12 is a schematic diagram showing an example of the sample volumes and the Doppler spectrum images.

FIG. 11 is a flow chart showing a process of forming a compound image of the Doppler spectrum images. The processing unit 130 may be configured to form the brightness mode image BI based on the brightness mode ultrasound data provided from the ultrasound data acquiring unit 120, at step S 1102 in FIG. 11. The brightness mode image BI may be displayed on a display unit 150.

The processing unit 130 may be configured to set the at least two sample volumes on the brightness mode image BI based on the input information provided from the user input unit 110, at step S1104 in FIG. 11. Thus, the ultrasound data acquiring unit 120 may be configured to transmit the ultrasound signals to the living body and receive the ultrasound echo signals from the living body to acquire the Doppler mode ultrasound data corresponding to the at least two sample volumes.

The processing unit 130 may be configured to form Doppler signals corresponding to each of the at least two sample volumes based on the Doppler mode ultrasound data provided from the ultrasound data acquiring unit 120, at step S1106 in FIG. 11. The methods of forming the Doppler signals are well known in the art. Thus, they have not been described in detail so as not to unnecessarily obscure the present disclosure.

For example, the processing unit 130 may form first Doppler signals corresponding to the sample volume $SV_1$ based on the first Doppler mode ultrasound data provided from the ultrasound data acquiring unit 120. The processing unit 130 may further form second Doppler signals corresponding to the sample volume $SV_2$ based on the second Doppler mode ultrasound data provided from the ultrasound data acquiring unit 120. The processing unit 130 may further form third Doppler signals corresponding to the sample volume $SV_3$ based on the third Doppler mode ultrasound data provided from the ultrasound data acquiring unit 120.

The processing unit 130 may be configured to form the at least two Doppler spectrum images corresponding to the at least two sample volumes based on the Doppler signals corresponding to the at least two sample volumes, at step S 1108 in FIG. 11. The methods of forming the Doppler spectrum image are well known in the art. Thus, they have not been described in detail so as not to unnecessarily obscure the present disclosure.

For example, the processing unit 130 may form a first Doppler spectrum image corresponding to the sample volume $SV_1$ based on the first Doppler signals corresponding to the sample volume $SV_1$. The processing unit 130 may further form a second Doppler spectrum image corresponding to the sample volume $SV_2$ based on the second Doppler signals corresponding to the sample volume $SV_2$. The processing unit 130 may further form a third Doppler spectrum image corresponding to the sample volume $SV_3$ based on the third Doppler signals corresponding to the sample volume $SV_3$.

The processing unit 130 may be configured to perform an image process for forming a compound image of the at least two Doppler spectrum images upon the at least two Doppler spectrum images to form the compound image, at step S1110 in FIG. 11. In one embodiment, the image process may include an image process for adding pixel values (i.e., brightness values) corresponding to pixels of same positions on the at least two Doppler spectrum images, an image process for subtracting the pixel values (i.e., brightness values) corresponding to the pixels of the same positions on the at least two Doppler spectrum images, an image process for multiplying the pixel values (i.e., brightness values) corresponding to the pixels of the same positions on the at least two Doppler spectrum images, an image process for performing various blending processes among the at least two Doppler spectrum images and the like.

Figure 13:
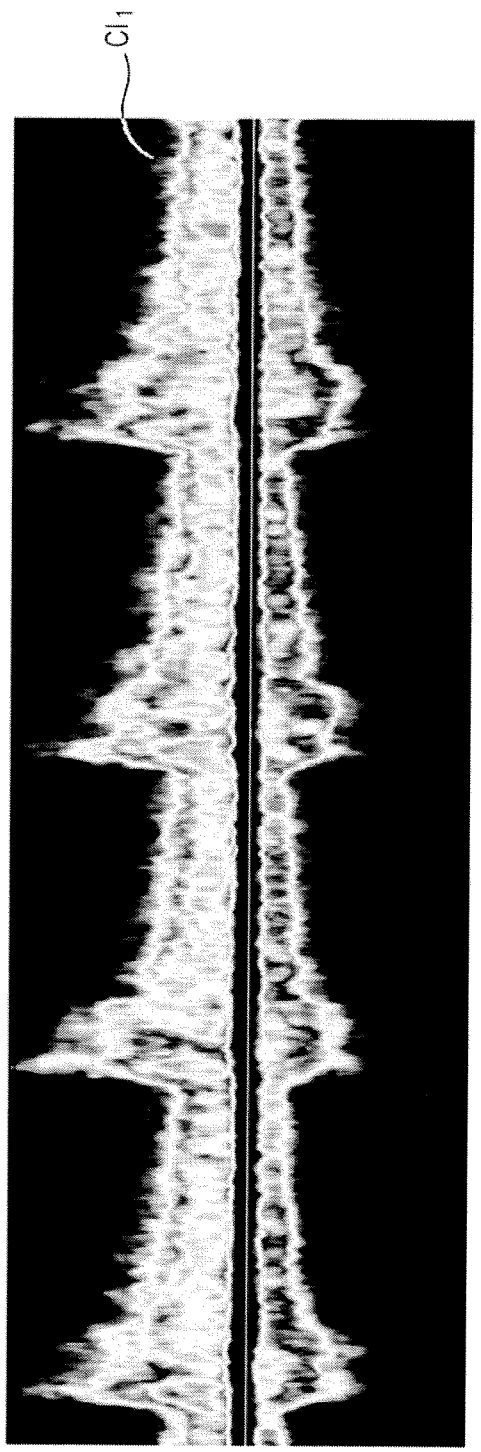
FIGS. 13 to 15 are schematic diagrams showing examples of the compound images.

As one example, the processing unit 130 may detect the pixels of the same positions on the first Doppler spectrum image to the third Doppler spectrum image, based on positions (orientation) of pixels corresponding to each of the first Doppler spectrum image to the third Doppler spectrum image. The processing unit 130 may further perform the image process for adding the pixel values corresponding to the detected pixels to form the compound image $CI_1$ as shown in FIG. 13.

Figure 14:
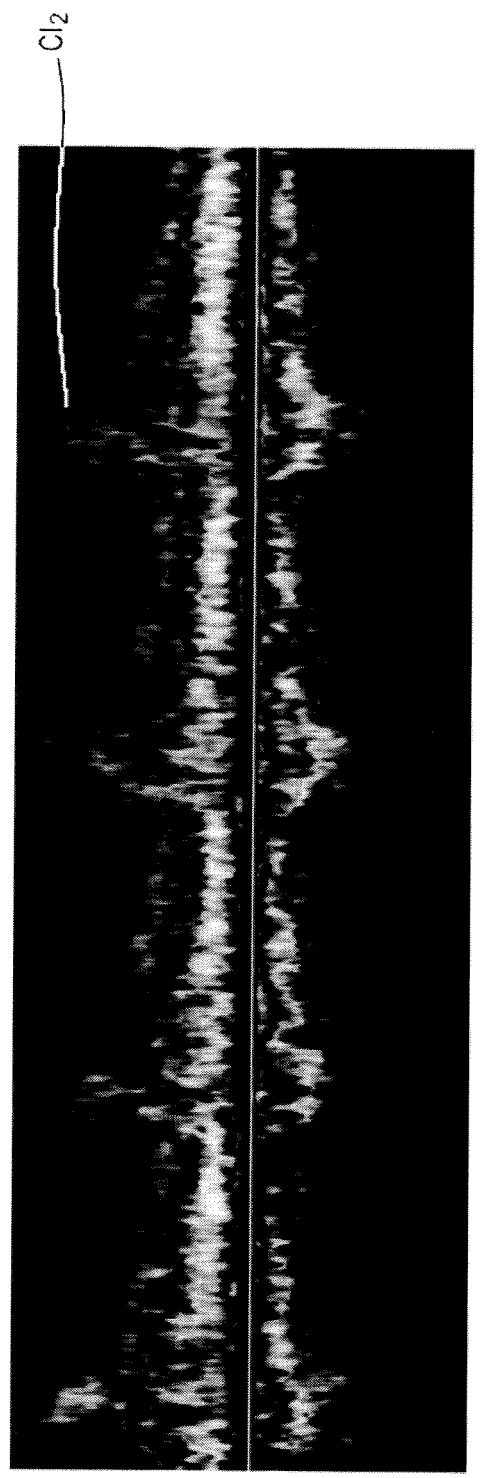

As another example, the processing unit 130 may detect the pixels of the same positions on the first Doppler spectrum image to the third Doppler spectrum image, based on the positions (orientation) of the pixels corresponding to each of the first Doppler spectrum image to the third Doppler spectrum image. The processing unit 130 may further perform the image process for subtracting the pixel values corresponding to the detected pixels to form the compound image $CI_2$ as shown in FIG. 14.

Figure 15:
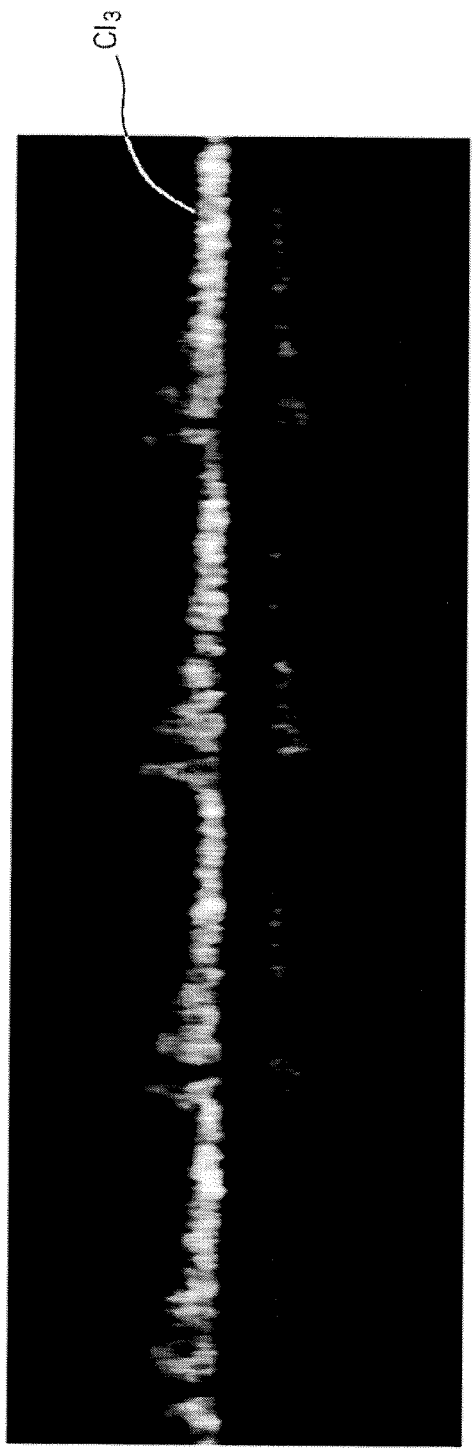

As yet another example, the processing unit 130 may detect the pixels of the same positions on the first Doppler spectrum image to the third Doppler spectrum image, based on the positions (orientation) of the pixels corresponding to each of the first Doppler spectrum image to the third Doppler spectrum image. The processing unit 130 may further perform the image process for multiplying the pixel values corresponding to the detected pixels to form the compound image $CI_3$ as shown in FIG. 15.

Optionally, the processing unit 130 may be configured to perform a men trace upon the compound image.

Referring back to FIG. 1, the ultrasound system 100 may further include the storage unit 140. The storage unit 140 may store the ultrasound data (i.e., brightness mode ultrasound data and Doppler mode ultrasound data) acquired by the ultrasound data acquiring unit 120. The storage unit 140 may further store the Doppler signals formed by the processing unit 130. The storage unit 140 may further store the input information received by the user input unit 110. The storage unit 140 may further store the brightness mode image, the Doppler spectrum images, and the compound image.

The ultrasound system 100 may further include the display unit 150. The display unit 150 may be configured to display the brightness mode image formed by the processing unit 130. The display unit 150 may be further configured to display the Doppler spectrum images formed by the processing unit 130. The display unit 150 may be further configured to display the compound image formed by the processing unit 130.

Although embodiments have been described with reference to a number of illustrative embodiments thereof, it should be understood that numerous other modifications and embodiments can be devised by those skilled in the art that will fall within the spirit and scope of the principles of this disclosure. More particularly, numerous variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. An ultrasound system, comprising: an ultrasound data acquiring unit, including an ultrasound probe, configured to transmit ultrasound signals to a living body in at least one transmission direction and receive ultrasound echo signals from the living body in at least one reception direction to acquire ultrasound data corresponding to a first sample volume and a second sample volume different from the first sample volume;
    a processor configured to form a first Doppler spectrum image corresponding to the first sample volume and a second Doppler spectrum image corresponding to the second sample volume based on the ultrasound data corresponding to the first sample volume and the second sample volume, the processor being further configured to perform an image process for forming a compound image upon the first Doppler spectrum image and the second Doppler spectrum image to form the compound image; and
    a display configured to display the compound image,
    wherein the image process includes at least one of a first image process for adding pixel values corresponding to pixels of same positions on the first Doppler spectrum image and the second Doppler spectrum image, a second image process for subtracting the pixel values corresponding to the pixels of the same positions on the first Doppler spectrum image and the second Doppler spectrum image, a third image process for multiplying the pixel values corresponding to the pixels of the same positions on the first Doppler spectrum image and the second Doppler spectrum image, and a fourth image process for performing a blending process among the pixels of the same position on the first Doppler spectrum image and the second Doppler spectrum image.

2. The ultrasound system of claim 1, wherein the ultrasound signals include unfocused signals or focused signals.

3. The ultrasound system of claim 1, wherein the ultrasound data acquiring unit is configured to:
    form reception signals based on the ultrasound echo signals;
    perform an analog-digital conversion upon the reception signals to form a plurality of sampling data;
    detect pixels corresponding to each of the sampling data from the pixels of the first Doppler spectrum image and the second Doppler spectrum image to cumulatively assign the sampling data to the detected pixels;
    perform reception beam-forming upon the sampling data assigned to the detected pixels to form reception-focused data corresponding to the first sample volume and the second sample volume; and
    form the ultrasound data corresponding to the first sample volume and the second sample volume based on the reception-focused data.

4. The ultrasound system of claim 3, wherein the ultrasound data acquiring unit is configured to:
    set a beam-forming curve for selecting pixels which the respective sampling data are used as pixel data thereof; and
    select the pixels corresponding to the beam-forming curve.

5. The ultrasound system of claim 3, wherein the ultrasound data acquiring unit is further configured to:
    determine pixels existing in the same column of the first Doppler spectrum image and the second Doppler spectrum image among the selected pixels;
    set weights corresponding to the respective determined pixels; and apply the weights to the sampling data of the respective determined pixels.

6. The ultrasound system of claim 5, wherein the ultrasound data acquiring unit is further configured to:
calculate distances from a center of the respective determined pixels to the beam-forming curve; and
set the weights based on the calculated distances.

7. The ultrasound system of claim 6, wherein the weights are set to be in proportional to or inverse proportional to the calculated distances.

8. The ultrasound system of claim 3, wherein the ultrasound data acquiring unit is further configured to:
set a sampling data set for selecting pixels which the respective sampling data are used as pixels data thereof among the sampling data; and
select pixels corresponding to respective sampling data of the sampling data set.

9. The ultrasound system of claim 3, wherein the ultrasound data acquiring unit is further configured to:
perform a down-sampling process upon the reception signals to form down-sampled data.

10. A method of providing a compound image, comprising:
a) forming a first Doppler spectrum image corresponding to a first sample volume and a second Doppler spectrum image corresponding to a second sample volume different from the first sample volume based on ultrasound data corresponding to the first sample volume and the second sample volume; and
b) performing an image process for forming a compound image upon the first Doppler spectrum image and the second Doppler spectrum image to form the compound image, wherein the image process includes at least one of a first image process for adding pixel values corresponding to pixels of same positions on the first Doppler spectrum image and the second Doppler spectrum image, a second image process for subtracting the pixel values corresponding to the pixels of the same positions on the first Doppler spectrum image and the second Doppler spectrum image, a third image process for multiplying the pixel values corresponding to the pixels of the same positions on the first Doppler spectrum image and the second Doppler spectrum image, and a fourth image process for performing a blending process among the pixels of the same position on the first Doppler spectrum image and the second Doppler spectrum image.

11. The method of claim 10, further comprising:
transmitting ultrasound signals to a living body including the target object in at least one transmission direction and receiving ultrasound echo signals from the living body in at least one reception direction to acquire the ultrasound data corresponding to the first sample volume and the second sample volume, prior to performing the step a).

12. The method of claim 11, wherein the ultrasound signals include unfocused signals or focused signals.

13. The method of claim 11, wherein the step of acquiring the ultrasound data, further comprises:
forming reception signals based on the ultrasound echo signals;
performing an analog-digital conversion upon the reception signals to form a plurality of sampling data;
detecting pixels corresponding to each of the sampling data from the pixels of the first Doppler spectrum image and the second Doppler spectrum image to cumulatively assign the sampling data to detected pixels;
performing reception beam-forming upon the sampling data assigned to the detected pixels to form reception-focused data corresponding to the first sample volume and the second sample volume; and
forming the ultrasound data corresponding to each of the first sample volume and the second sample volume based on the reception-focused data.

14. The method of claim 13, wherein the step of detecting the pixels corresponding to each of the sampling data, comprises:
setting a beam-forming curve for selecting pixels which the respective sampling data are used as pixel data thereof; and
selecting the pixels corresponding to the beam-forming curve.

15. The method of claim 14, wherein the step of acquiring the ultrasound data, further comprises:
determining pixels existing in the same column of the first Doppler spectrum image and the second Doppler spectrum image among the selected pixels;
setting weights corresponding to the respective determined pixels; and
applying the weights to the sampling data of the respective determined pixels.

16. The method of claim 15, wherein the step of setting the weights, comprises:
calculating distances from a center of the respective determined pixels to the beam-forming curve; and
setting the weights based on the calculated distances.

17. The method of claim 16, wherein the weights are set to be in proportional to or inverse proportional to the calculated distances.

18. The method of claim 14, wherein the step of detecting the pixels corresponding to each of the sampling data, further comprises:
setting a sampling data set for selecting pixels, which the respective sampling data are used as pixel data thereof, among the sampling data; and
selecting pixels corresponding to respective sampling data of the sampling data set.

19. The method of claim 14, wherein the step of detecting the pixels corresponding to each of the sampling data, further comprises:
performing a down-sampling process upon the reception signals to form down-sampled data.

* * * * *